US009315866B2

(12) United States Patent
Meijer et al.

(10) Patent No.: US 9,315,866 B2
(45) Date of Patent: Apr. 19, 2016

(54) COMBINATION OF MAL AND CADM1 MARKERS FOR HPV INDUCED INVASIVE CANCERS AND THEIR HIGH-GRADE PRECURSOR LESIONS

(75) Inventors: Christophorus Joannes Lambertus Maria Meijer, Leiden (NL); Petrus Josephus Ferdinandus Snijders, Amstelveen (NL); Renske Daniëla Maria Steenbergen, Amsterdam (NL)

(73) Assignee: VERENIGING VOOR CHRISTELIJK HOGER ONDERWIJS, WETENSCHAPPELIJK ONDERZOEK EN PATIENTENZORG, Amsterdam (NL)

( * ) Notice: Subject to any disclaimer, the term of this patent is extended or adjusted under 35 U.S.C. 154(b) by 919 days.

(21) Appl. No.: 12/937,981

(22) PCT Filed: Apr. 14, 2009

(86) PCT No.: PCT/NL2009/050194
§ 371 (c)(1),
(2), (4) Date: Jan. 3, 2011

(87) PCT Pub. No.: WO2009/128714
PCT Pub. Date: Oct. 22, 2009

(65) Prior Publication Data
US 2011/0104660 A1 May 5, 2011

(30) Foreign Application Priority Data
Apr. 14, 2008 (EP) .................... 08154496

(51) Int. Cl.
C12Q 1/68 (2006.01)
C12Q 1/70 (2006.01)
G01N 33/53 (2006.01)

(52) U.S. Cl.
CPC ............... *C12Q 1/6886* (2013.01); *C12Q 1/68* (2013.01); *C12Q 1/70* (2013.01);
(Continued)

(58) Field of Classification Search
None
See application file for complete search history.

(56) References Cited

U.S. PATENT DOCUMENTS

2006/0211009 A1* 9/2006 An et al. ............... 435/6
2006/0252029 A1* 11/2006 Meijer et al. ............ 435/5
(Continued)

FOREIGN PATENT DOCUMENTS

WO WO-2004/087962 10/2004
WO WO-2007/007205 1/2007

OTHER PUBLICATIONS

Wong et al., "Genome-wide gene expression profiling of cervical cancer in Hong Kong women by oligonucleotide microarray," International Journal of Cancer, vol. 118, No. 10, pp. 2461-2469 (2006).*
(Continued)

*Primary Examiner* — Benjamin P Blumel
*Assistant Examiner* — M. Franco Salvoza
(74) *Attorney, Agent, or Firm* — Morrison & Foerster LLP

(57) ABSTRACT

The inventors now have developed a (molecular) diagnostic marker based on MAL alterations, in particular reduced MAL mRNA and protein expression as well as MAL promoter hypermethylation, to identify human papillomavirus (HPV)-induced high-grade precancerous lesions such as premalignant cervical lesions of invasive cervical cancer, and high-risk human papillomavirus (HPV)-induced precursor lesions of non-cervical invasive cancers within, cell material obtained via scraping, lavage or by other means and/or tissue. In particular, the present invention relates to the use of the MAL gene (including its promoter) and the gene products thereof as marker for HPV-induced high-grade premalignant lesions, allowing early detection and better treatment option for the individual patient.

17 Claims, 2 Drawing Sheets

(52) U.S. Cl.
CPC ... *C12Q 2523/125* (2013.01); *C12Q 2600/112* (2013.01); *C12Q 2600/154* (2013.01); *C12Q 2600/156* (2013.01); *C12Q 2600/158* (2013.01)

(56) References Cited

U.S. PATENT DOCUMENTS

2011/0171628 A1* 7/2011 Meijer et al. .................. 435/5
2011/0189653 A1* 8/2011 Van Criekinge et al. ......... 435/5

OTHER PUBLICATIONS

Buffart et al., "MAL promoter hypermethylation as a novel prognostic marker in gastric cancer," British Journal of Cancer, 99: pp. 18-02-1807 (2008).*
Reamon-Buettner et al., "Epigenetic silencing of cell adhesion molecule 1 in different cancer progenitor cells of Transgenic c-Myc and c-Raf Mouse Lung Tumors," Cancer Res 68, pp. 7587-7596 (2008).*
Wentzensen et al., "Utility of methylation markers in cervical cancer early detection: Appraisal of the state of the science," Gynecologic Oncology 112, pp. 293-299 (2009).*
Overmeer et al., "Association between dense CADM1 promoter methylation and reduced protein expression in high-grade CIN and cervical SCC," Journal of Pathology 215: pp. 388-397 (2008).*
Rancano et al., "Alternative Splicing of Human T-Cell-Specific MAL mRNA and Its Correlation with the Exon/Intron Organization of the Gene," Genomics 21, pp. 447-450 (1994); NCBI Nucleotide BLAST Search showing Rancano et al., X76681.1 (attached).*
Martinez et al., "Identification of differentially expressed genes in HPV-positive and HPV-negative oropharyngeal squamous cell carcinomas," Eur J Cancer 43(2): 415-432 (2007).*
Lind et al., "Hypermethylated MAL gene—a silent marker of early colon tumorigenesis," Journal of Translational Medicine 6:13 (2008).*
Hatta et al., The Journal of Obstetrics and Gynecology Research (2004) 30(1):53-58.
Henken et al., British Journal of Cancer (2007) 97(10):1457-1464.
International Search Report for PCT/NL2009/050194, mailed on Jul. 29, 2009, 4 pages.
International Preliminary Report on Patentability for PCT/NL2009/050194, issued Oct. 19, 2010, 8 pages.
Mimori et al., Oncogene (2003) 22(22):3463-3471.
Steembergen et al., Journal of the National Cancer Institute (2004) 96(4):294-305.
Wong et al., International Journal of Cancer (2006) 118(10):2461-2469.

* cited by examiner

MAL promoter, coding sequence, CpG rich sequence of intron 1 and 3'UTR

Taken from UCSC genome bioinformatics
Ref: hg18_knownGene_uc002stx.1 range=chr2:95054206-95083462

Transcription start is indicated in bold
The coding sequence is in upper case
Part of intron 1, containing CpG rich sequences and being part of a larger CpG island starting in the promoter (nt375), is marked by * and underlined

```
gactcgggcggatttcaggcttcagtgtttgtaggaggaaacacagcaat
cacactattaatagtaaattaaaataaatgggcaactgctgcatggtaat
actttttttttaaggcaaaaataaaaaatagtgaaacagagaaacaaa
acatgaaacacggcagtcaacaggcaggcaaagaacctggggtgggg
tagcagcggtcccaccctcaaaaggccgggctgcccagaccaagagaaa
gcgatgaatctcttctggtaacgtccttcctgtcgcatggattcaggc
cgacctgcccagcaccaccaccagcagccttctgctggggccggcacag
ctgggagcaacctcctactctcaggcagacgcgcagcaccaagcagagag
gcccggtgcaggatccagcgcgaaccagcgccagtcgacgcgg
aaggggcggcggccgcgggccggtcccatcaccccactgcagaccccaga
ctgtggcggtggtccagttccgccaggaaacgcgcgcctggagctgtggg
tcgcgcacattaatcgcatccagcgggaaaatgaaggagcccaaattcaa
agttaaagtaatggtgacccgagaggtgccttgatgagaaggtttgggt
cccggttactgatggttatcattcttacgagatgctggtcacctacgaag
ggagaaagcacgaggagcgcctgaccaaagtggttttgccctgcttcca
gcaagaggtggcacccacggctggaacgcaggagtgcagcccacagtccc
cagctctggacgcccgcagcggggcctgaagagagttcaggcgggtgccc
gcgggcgctcggagcgggtctccggggcgtggggcaggggcgggggttgg
gcgggggccgggggtcctccctcttatgcccgggctcccctgctcttaa
cccgcgcgcgggggcgcccaggccactgggctcgcgggagccagcgagag
gtatgcgcggagtctgagcggcgctcgtcccgtcccaaggccgacgcag
caagcgtcATGGCCCCCGCAGCGGCGACGGCGGCAGCACCCTGCCCAG
TGGCTTCTCGGTCTTCACCACCTTGCCCGACTTGCTCTTCATCTTTGAGT
TT*gtgagtggctcctgccggggaagggacggggtgggctgagccgtacg
ctctctcgggcgccagcacagctgtcgacggatccgctagctgcaca
ggtctggagcgctcgggcagcagcgcagggcgggactaagccaggg
aagtcccctcccacctcgggtccttgtgccctctagaccaacagaatg
aggggaacagtctacaggactatgaaggaaaactggttcccaactggg
gtcagatgtaggcagccggcaggggggacggctcttggttcgctggtc
ccaaagctgcgccggggggccaacttgacgcgcgcagcgccaccgaagctc
ccgccgcgcttgcgcggttgggtagaagtgcgcagcttttacaggag
aaggtttcgttaaaaagaaaaaaaatcagcaagagaaacattagtatt
accaagcgagatttggagatgagagtgagctgaatccggtttattttctt
ctggcctttaaagtttctggcgaggaacgtatttacgaccaattcgat
ctggaaatgaggccatcgtttgcttggccgcagtccttctgccccgtgtg
cagggtggaggtggaggagatagagggtggggctgggggtgccggca
gagcgatccgagcgcctgactgaccttgggcaggccgggcctctgca
gctgcggtcgtccgccttgcaggcacgtctctgcctgaggctgcaga
aaagcgcttcctactgagaactcctgataagcgctcacggtgtcgcgaag
ccgaagtgacctcctcagcctcaactcccggggccgctggccttcac*
ATCTTCGGGCCTGGTGTGGATCTGGTGCCCTCCTCCCTGGTGCCC
TGGCCCCTGGTCCAGGGCTGGGTGATGTTCGTGTCTGTGTTCTGCTTCGT
GGCCACCACCACCTTGATCATCCTGTACATAATTGGAGCCCACGGTGGAC
AGACTTCCTGGGTCACCTTGGACGCAGCCTACCACTGCACCGCTGCCCTC
```

FIG.1A

TTTTACCTCAGCGCCTCAGTCCTGGAGGCCCTGGCCACCATCACGATGCA
AGACGGCTTCACCTACAGGCACTACCATGAAAACATTNCTGCCGTGGTGT
TCTCCTACATAGCCACTCTGCTCTACGTGGTCCATGCGGTGTCTCTCTTTA
ATCAGATGGAAGTCTTCATAAagccgcagtagaacttgagctgaaaccc
agatggtgttaactggccgccccactttccggcataacttcttagaaaac
agaaatgcccttgatggtggaaaaaagaaaacaccacccccccctgcc
caaaaaaaaagcccctgcctgttgctcgtgggtgctgtgtttactctcc
cgtgtgcttcgcgtccggggttgggagcttgctgtgtctaacctccaact
gctgtgctgtctgctagggtcacctcctgtttgtgaaagggacttctt
gttcgtgggtgggaagtggcgaccgtgacctgacgaaggaagaaagatcc
tctgctgaccctggagcagctctcgagaactacctgttggtattgtccc
caagctctcccgagcgccccatcttgtgccatgttttaagtcttcattgga
tgttctgcatgtcatgggactaaaactcacccaacagatcttttccagag
gtccatggtggaagacgatacccctgtgaaatactttataaaatgtctta
atgttc

COMBINATION OF MAL AND CADM1 MARKERS FOR HPV INDUCED INVASIVE CANCERS AND THEIR HIGH-GRADE PRECURSOR LESIONS

CROSS-REFERENCE TO RELATED APPLICATIONS

This application is the national phase of PCT application PCT/NL2009/050194 having an international filing date of 14 Apr. 2009, which claims benefit of European application No. 08154496.7 filed 14 Apr. 2008. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 313632010500Seqlist.txt | Dec. 30, 2010 | 4,315 bytes |

FIELD OF THE INVENTION

The invention relates to the field of cancer prevention and medical diagnostics; and is concerned with a molecular diagnostic marker for human papillomavirus (HPV)-induced invasive cancers and high-grade precursor lesions thereof, such as invasive cervical cancer and premalignant cervical lesions. In particular, the present invention relates to the use of the MAL genomic and regulatory sequence or the gene products thereof as marker for hrHPV-induced premalignant lesions with invasive potential and hrHPV-induced invasive cancers.

BACKGROUND OF THE INVENTION

Cancer of the uterine cervix is the second most common cancer in women world-wide and is responsible for approximately 250,000 cancer deaths a year.

Cervical squamous cell carcinoma development is characterized by a sequence of premalignant lesions, so-called cervical intraepithelial neoplasia (CIN), which are graded 1 to 3, referring to mild dysplasia (CIN 1), moderate dysplasia (CIN 2) and severe dysplasia/carcinoma in situ (CIN 3), respectively. CIN 1 is also referred to as low grade squamous intraepithelial lesion (LSIL) and CIN 2 and CIN 3 together as high grade squamous intraepithelial lesion (HSIL) For cervical adenocarcinoma, adenocarcinoma in situ (ACIS) is an established precursor lesion. In principle, these premalignant lesions are reversible, although the more severe the lesion, the lower the chance of spontaneous regression. Cervical cancer is considered a preventable disease because the premalignant stages can be detected by exfoliative cytology and treated relatively easily when necessary, with only minor side effects. Cervical screening is aimed to early diagnose the high-grade premalignant (i.e., CIN 2/3 and adenocarcinoma in situ) and treatable cancerous lesions, thereby reducing the mortality of invasive cervical cancer. General medical practice comprises the treatment of all women with morphologically confirmed CIN 2, CIN 3 and adenocarcinoma in situ, in order to prevent the development of cervical cancer.

Over the past decade it has been well established that cervical carcinogenesis is initiated by an infection with high-risk human papillomavirus (hrHPV). Expression of the viral oncogenes E6 and E7, which disturb the p53 and Rb tumor suppressor pathways, respectively, has been shown to be essential for both the onset of oncogenesis and the maintenance of a malignant phenotype. Therefore, testing for hrHPV appeared as an attractive, primary screening tool. However, consistent with a multistep process of carcinogenesis, additional alterations in the host cell genome are required for progression of an hr-HPV infected cell to invasive cancer cell. Only a small proportion of women infected with high-risk HPV will develop high-grade premalignant cervical lesions (CIN 2/3) and, if left untreated, cervical cancer. In most women with premalignant cervical lesions the lesions regress spontaneously. Of the women who participate in population based screening about 5-6% have a positive hrHPV test (Bulkmans et al., Int J Cancer 2004, 110:94-101). However, only at maximum 20% of them (1% of the participating women) have ≥CIN 2/3. Therefore, primary screening by hrHPV testing will be accompanied with a substantial number of redundant follow-up procedures and unnecessary anxiety amongst women, unless markers can be applied to the cervical smears that allow stratification of hrHPV positive women for risk of ≥CIN 2/3 and ≥adenocarcinoma in situ.

A major challenge is to reduce the percentage of test positive women to those that have clinically meaningful lesions. One mode is to use cytology as a secondary (so-called triage) test for hrHPV positive women. Still, this leaves a substantial number of hrHPV positive women with normal cytology (3.5% of the women in the screening population), of which 10% have or acquire ≥CIN 3. Moreover, cytology is not an option for self-sampled cervico-vaginal specimens that can be taken at home, since these are not representative for the cytological status of the cervix (Brink et al., 2006, J. Clin. Microbiol. 44:2518-2523). Therefore, there is a need for supplementary or alternative triage tools to stratify hrHPV positive women into those with and without ≥CIN 2/3 and ≥adenocarcinoma in situ.

SUMMARY OF THE INVENTION

The inventors now have developed a (molecular) diagnostic marker based on MAL alterations, in particular reduced MAL mRNA and protein expression as well as MAL promoter hypermethylation, to identify human papillomavirus (HPV)-induced high-grade precancerous lesions such as premalignant cervical lesions of invasive cervical cancer, and high-risk human papillomavirus (HPV)-induced precursor lesions of non-cervical invasive cancers within, cell material obtained via scraping, lavage or by other means and/or tissue. In particular, the present invention relates to the use of the MAL gene (including its promoter) and the gene products thereof as marker for HPV-induced high-grade premalignant lesions, allowing early detection and better treatment option for the individual patient.

It has now surprisingly been found that the gene encoding T-lymphocyte maturation associated protein, also known as T-cell differentiation protein (further referred to as MAL; Genbank Accession NM_002371) is involved as a tumor suppressor gene in cervical carcinogenesis, and that a low level of expression of the MAL gene, mainly caused by MAL promoter methylation, is an important determinant of cervical carcinogenesis. The MAL genomic and regulatory sequences and the gene products thereof thus provide valuable markers to diagnose invasive cervical cancer and the high-grade precursor lesions thereof. Particularly when combined with methylation analysis of CADM1 (Genbank ID NM_014333.3) high sensitivity for invasive cervical cancer and the high-grade precursor lesions thereof is achieved, which exceeds that found with cervical cytology. Additionally, the present invention is suited to diagnose non-cervical hrHPV-associated invasive cancers and their high-grade precursor lesions.

Cervical cancer is almost exclusively associated with human papillomavirus (HPV) infection. Human papillomaviruses, constitute a group of more than 100 types of viruses, as identified by variations in DNA sequence. The various HPVs cause a variety of cutaneous and mucosal diseases. HPVs are broadly classified into low-risk and high-risk types, based on their ability to induce malignant changes in infected cells. Low risk HPV types such as 1, 2, 4, 6, 11, 13 and 32 are primarily associated with benign lesions or common warts, while the high risk types, such as 16, 18, 31, 33, 35, 39, 45, 51, 52, 56, 58, 59, 66, and 68 are primarily associated with premalignant and malignant epithelial lesions. These high-risk types of HPV cause growths that are usually flat and nearly invisible, as compared with the warts caused by low-risk types, e.g. HPV-6 and HPV-11. The high-risk HPV types have been found to cause invasive carcinoma of the uterine cervix, as well as invasive carcinoma elsewhere in the anogenital tract and/or head-neck region. Therefore, the present invention is not only suited to detect invasive cervical cancer and precursor stages thereof associated with T-lymphocyte maturation associated protein (MAL), but also other invasive cancers and corresponding precursor stages that are induced by HPV, particularly of the high-risk type. Thus, the present invention provides a method for the risk assessment of any HPV-induced high-grade premalignant lesion or invasive cancer.

Accordingly, the present invention provides methods as defined in claim 1 of detecting HPV-induced high-grade precursor lesions and HPV-induced invasive cancers associated with T-lymphocyte maturation associated protein (MAL) in a subject in need thereof, said method comprising contacting a cell component of a test cell of the subject with a reagent that detects the level of the cell component in the test cell and determining a modification in the level of the cell component in the test cell as compared with a comparable healthy cell, wherein the cell component indicates the level of MAL in the cell and the modification indicates the presence of HPV-induced precancerous lesions or HPV-induced invasive cancer.

Very suitable HPV-induced precursor lesions and invasive cancers in the context of the present invention are cervical precancerous lesions and invasive cervical cancers, but also precursor lesions and invasive cancers induced by high-risk HPV in other tissues such as oral cavity, oropharynx, anus, rectum, penis, vulva, vagina etc.

A test cell may be a (pre)neoplastic cell, a proliferating cervical cell, or any other cell wherein the presence of an HPV-induced precursor lesion with invasive potential and HPV-induced invasive cancer associated with T-lymphocyte maturation associated protein (MAL) is to be detected.

In another embodiment, the present invention provides methods as defined in claim 1 of detecting HPV-induced precursor lesion with invasive potential or HPV-induced invasive cancer associated with T-lymphocyte maturation associated protein (MAL) in a subject in need thereof, said method comprising contacting a target cellular component of a test cell with a reagent that detects MAL and detecting an alteration in MAL as compared to that of a comparable normal cell, preferably in said detection an increased methylation of the MAL promoter and CpG rich intronic sequences in the test cell and/or a reduced production of MAL in the test cell as compared to the comparable normal cell is determined.

In another aspect, the present disclosure relates to the use of molecular diagnostic markers as defined in claim 13 for the detection of HPV-induced high-grade precursor lesion and HPV-induced invasive cancer associated with T-lymphocyte maturation associated protein (MAL), wherein said marker indicates MAL promoter methylation and/or expression of mRNA associated with production of MAL polypeptide. By such use, presence of a high-grade precancerous lesion or invasive cancer may be predicted.

BRIEF DESCRIPTION OF THE DRAWINGS

FIG. 1A-B (SEQ ID NO:1) shows the MAL5' regulatory region, coding sequence, CpG rich part of first intronic sequence and transcribed 3' non-coding sequences.

DETAILED DESCRIPTION OF THE INVENTION

"Expression" refers to the transcription of a gene into structural RNA (rRNA, tRNA) or messenger RNA (mRNA) and, if applicable, subsequent translation into a polypeptide or protein.

The term "HPV-induced invasive cancer" refers to a carcinoma induced by high-risk HPV, which invades surrounding tissue. This includes all HPV-induced carcinoma histotypes, i.e., squamous cell carcinomas, adenocarcinomas, adenosquamous carcinomas and neuroendocrine carcinomas. in relevant organs such as cervix, oral cavity, oropharynx, anus, rectum, penis, vulva, vagina etc.

The term "invasive cervical cancer" refers to a cervical carcinoma invading surrounding tissue. This includes all carcinoma histotypes, i.e., squamous cell carcinomas, adenocarcinomas, adenosquamous cell carcinomas and neuroendocrine carcinomas.

The terms "premalignant lesion" and "precursor lesion" refer to a stage in the multistep cellular evolution to cancer with a strongly increased chance to progress to a carcinoma. With classical morphology the pathologist is unable to predict in the individual patient which of these lesions will progress or regress. The current patent refers to a method, which can predict invasive cancer or a high-grade precursor lesion thereof.

The term "high-grade premalignant cervical lesion" refers to a stage in the multistep cellular evolution to cervical cancer with a strongly increased chance to progress to a cervical carcinoma. The term "capable of specifically hybridizing to" refers to a nucleic acid sequence capable of specific base-pairing with a complementary nucleic acid sequence and binding thereto to form a nucleic acid duplex.

A "complement" or "complementary sequence" is a sequence of nucleotides which forms a hydrogen-bonded duplex with another sequence of nucleotides according to Watson-Crick base-paring rules. For example, the complementary base sequence for 5'-AAGGCT-3' is 3'-TTCCGA-5'.

The term "stringent hybridization conditions" refers to hybridization conditions that affect the stability of hybrids, e.g., temperature, salt concentration, pH, formamide concentration and the like. These conditions are empirically optimised to maximize specific binding and minimize non-specific binding of the primer or the probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of a complementary target sequence hybridises to a perfectly matched probe or primer. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel et al, Current Protocols in Molecular Biology, John Wiley & Sons Inc., 1994.

The term "oligonucleotide" refers to a short sequence of nucleotide monomers (usually 6 to 100 nucleotides) joined by phosphorous linkages (e.g., phosphodiester, alkyl and arylphosphate, phosphorothioate), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming stable secondary structures (e.g., stem-and-loop and loop-stem-loop structures).

The term "primer" as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxy ribonucleotide. The primer must be sufficiently long to prime the synthesis of extension products in the presence of the agent for polymerization. The exact lengths of the primers will depend on many factors, including temperature and source of primer. A "pair of bi-directional primers" as used herein refers to one forward and one reverse primer as commonly used in the art of DNA amplification such as in polymerase chain reaction (PCR) amplification.

The term "probe" refers to a single-stranded oligonucleotide sequence that will recognize and form a hydrogen-bonded duplex with a complementary sequence in a target nucleic acid sequence analyte or its cDNA derivative.

The MAL (T-lymphocyte maturation associated protein) gene (Genbank Accession NM_002371) has originally been identified as a differentially expressed gene during T-cell development (Alonso and Weisman 1987, Proc. Natl. Acad. Sci. USA, 84, 1997-2001). MAL encodes as 17 kDa integral membrane protein and is a component of glycolipid enriched membrane microdomains or rafts (Kim et al. 1995, J. Neurosci. Res., 42, 413-422). MAL has an essential role as a component of the protein machinery for apical transport of membrane and secretory proteins in polarized epithelial cells (Cheong et al., 1999, Proc. Natl. Acad. Sci. USA, 84, 6241-6248).

Reduced MAL expression has been detected in a various number of human cancers, including esophageal, gastric and colorectal cancer (Mimori et al., 2003, Oncogene, 22, 3463-3471; Mimori 2007 et al., Ann. Surg. Oncol., 14, 1670-1677)

In colorectal cancer MAL downregulation has been associated with promoter hypermethylation (Mori et al, 2006, Gastroenterology, 131, 797-808; Lind et al., 2007 Gastroenterology, 132, 1631-1632)

A functional role of MAL acting as a tumor suppressor gene was demonstrated by re-expression of the MAL gene in esophageal cancer cells, resulting in a suppression of motility, invasion and tumorigenicity, while enhancing apoptosis (Mimori et al., 2003, Oncogene, 22, 3463-3471)

The present inventors have now established that alterations in MAL, including MAL promoter methylation and reduced MAL expression is a frequent event in cervical carcinomas of both squamous cell carcinoma, adeno-sqamous carcinoma, adenocarcinoma and neuroendocrine carcinoma histotypes, and their high-grade precursor lesions. In vitro studies revealed a functional involvement of MAL inactivation in cervical cancer development, as MAL overexpression in cells of the HPV 16 containing SiHa cervical cancer cell line reduced proliferation and suppressed anchorage independent growth. Most interestingly, the present inventors have shown that not only hypermethylation of the MAL promoter but, remarkably, also reduced mRNA expression can be detected in cervical scrape samples and predict the presence of a high-grade CIN lesion or invasive carcinoma. In addition, MAL promoter methylation could be detected in cervical-vaginal specimens collected by self-sampling and was found to be associated with the presence of an underlying high-grade CIN lesion or invasive cervical cancer.

Interestingly, by combining methylation analysis of MAL with one newly selected promoter region of CADM1 (Genbank ID NM_014333.3) a high sensitivity for ≥CIN 2 is reached that exceeds that of cytology. Moreover, unlike cytology, methylation analysis for both genes can also be successfully performed on self-sampled, cervical-) vaginal and vulvar specimens. These results indicate that the detection of MAL promoter methylation either or not in combination with reduced MAL expression or CADM1 promoter methylation in cervical scrapes and self-collected cervical-vaginal specimens can predict high-grade CIN disease or cervical cancer.

Accordingly, the present invention provides methods as defined in claim 1 of detecting HPV-induced high-grade precancerous lesions and HPV-induced invasive cancers associated with T-lymphocyte maturation associated protein (MAL) in a subject in need thereof, or indicative thereof, said method comprising contacting a cell component of a test cell of the subject with a reagent that detects the level of the cell component in the test cell and determining a modification in the level of the cell component in the test cell as compared with a comparable healthy cell, wherein the cell component indicates the level of MAL in the cell and the modification indicates the presence of HPV-induced precursor lesions with invasive potential and HPV-induced invasive cancers.

The test cell of the subject may comprise a cell from a sample of mucosal cells, such as cervical cells, and also other tissue such as oral cavity, oropharynx, penis, vulva, anus, rectum and other tissues wherein a precursor lesion or cancer associated with HPV is to be detected. All such samples may be used as a sample in a method of the present invention. Preferably, a sample of a patient's cells comprise cervical cells as test cells. The cervical cells may e.g. be presented as a histological or cytological specimen. Cytological specimens comprise conventional cervical smears as well as thin layer preparations of cervical specimens and cervico-vaginal or vaginal specimens collected by self-sampling.

A method of the present invention is particularly suited for the detection of high-grade precancerous lesions and invasive cancers associated with T-lymphocyte maturation protein (MAL) that are induced by high-risk HPVs. A method of detecting HPV-induced high-grade precancerous lesions and HPV-induced invasive cancers associated with T-lymphocyte maturation associated protein (MAL) may accordingly relate to the measurement of MAL expression, such as in the form of measuring MAL gene transcripts and/or subsequent proteins translated from said transcripts. Also a method of detecting HPV-induced high-grade precancerous lesions with invasive potential and HPV-induced invasive cancers may comprise measuring MAL promoter methylation as an indication of MAL expression capacity and/or MAL protein production capacity.

FIG. 1 shows the CpG-rich promoter region and CpG-rich first intronic sequence of the MAL gene as well as the coding sequence and transcribed 3' non-coding sequence. Methylation of the CpG-rich sequences particularly in the promoter region will result in a sharply decreased transcription or even complete blockage of transcription. Therefore, the promoter region provides a positive marker sequence for the expression potential of this gene. Alternatively, the expression of the MAL gene may be detected by measuring gene transcripts. As such, the coding region for the MAL protein in this gene provides a marker sequence for detection of transcripts of the gene. In yet another alternative, the expression of the MAL gene may be detected by measuring MAL protein directly.

The test cell component contacted can thus be nucleic acid, such as DNA or RNA, preferably mRNA, or protein. When a cell component is protein, the reagent is typically an anti-MAL antibody. When the component is nucleic acid, the reagent is typically a nucleic acid (DNA or RNA) probe or (PCR) primer. By using such probes or primers, gene expression products, such as mRNA may for example be detected. Alternatively, when the component is nucleic acid, the reagent may also be a restriction endonuclease, preferably a methylation sensitive restriction endonuclease for the detection of the presence of methyl groups on the test cell nucleic acid, said test cell nucleic acid then preferably being DNA.

The test cell component may be detected directly in situ or it may be isolated from other cell components by common methods known to those of skill in the art before contacting with the reagent (see for example, "Current Protocols in Molecular Biology", Ausubel et al. 1995. 4th edition, John Wiley and Sons; "A Laboratoty Guide to RNA: Isolation, analysis, and synthesis", Krieg (ed.), 1996, Wiley-Liss; "Molecular Cloning: A laboratory manual", J. Sambrook, E. F. Fritsch. 1989. 3 Vols, 2nd edition, Cold Spring Harbor Laboratory Press)

Detection methods include such analyses as Southern and Northern blot analyses, RNase protection, immunoassays, in situ hybridization, PCR (Mullis 1987, U.S. Pat. Nos. 4,683, 195, 4,683,202, en 4,800,159), LCR (Barany 1991, Proc. Natl. Acad. Sci. USA 88:189-193; EP Application No., 320, 308), 3SR (Guatelli et al., 1990, Proc. Natl. Acad. Sci. USA 87:1874-1878), SDA (U.S. Pat. Nos. 5,270,184, en 5,455, 166), TAS (Kwoh et al., Proc. Natl. Acad. Sci. USA 86:1173-1177), Q-Beta Replicase (Lizardi et al., 1988, Bio/Technology 6:1197), Rolling Circle Amplication (RCA) or other methods for the amplification of DNA. In an alternative method RNA may be detected by such methods as NASBA (L. Malek et al., 1994, Meth. Molec. Biol. 28, Ch. 36, Isaac PG, ed., Humana Press, Inc., Totowa, N.J.) or TMA.

Nucleic acid probes, primers and antibodies can be detectably labeled, for instance, with a radioisotope, a fluorescent compound, a bioluminescent compound, a chemiluminescent compound, a metal chelator, an enzyme or a biologically relevant binding structure such as biotin or digoxygenin. Those of ordinary skill in the art will know of other suitable labels for binding to the reagents or will be able to ascertain such, using routine experimentation.

Other methods for detection include such analyses as can be performed with nucleic acid arrays (See i.a. Chee et al., 1996, Science 274(5287):610-614). For example, DNA arrays may be used for the detection of nucleic acids according to the invention. Such arrays comprise oligonucleotides with sequences capable of hybridizing under stringent conditions to the nucleic acid cell component of which the level is detected in a method of the present invention.

Since the present invention shows that a decreased level of MAL transcription is often the result of hypermethylation of the MAL gene, it is often desirable to directly determine whether the MAL gene is hypermethylated. In particular, the cytosine rich areas termed "CpG islands", which are primarily situated in the 5' regulatory regions of genes are normally unmethylated. The term "hypermethylation" includes any methylation of cytosine at a position that is normally unmethylated in the MAL gene sequence (e.g. the MAL promoter, first exon and first intronic sequence, see FIG. 1). Hypermethylation can for instance be detected by restriction endonuclease treatment of the MAL polynucleotide (gene) and Southern blot analysis. Therefore, in an invention method wherein the cellular component detected is DNA, restriction endonuclease analysis is preferred to detect hypermethylation of the MAL gene. Any restriction endonuclease that includes CG as part of its recognition site and that is inhibited when the C is methylated, can be utilized. Methylation sensitive restriction endonucleases such as BssHII, MspI, NotI or HpaII, used alone or in combination, are examples of such endonucleases. Other methylation sensitive restriction endonucleases will be known to those of skill in the art.

Other methods for the detection of MAL promoter hypermethylation involve bisulfite modification of DNA, in which the unmethylated cytosines are converted to an uracil whereas the methylated cytosines are protected from chemical modification. Subsequent PCR amplification and sequencing will reveal whether cytosines in CpG islands are maintained in case of methylation or replaced by a uracil in case of an unmethylated status. Another method involves the treatment a PCR amplified product generated from bisulfite modified DNA with restriction endonuclease that includes CG as part of its recognition site.

An alternative means to test for methylated sequences is a methylation specific PCR, which is also based on bisulfite modification of DNA, followed by specific PCR reactions that target CpG rich sequences.

For purposes of the invention, an antibody (i.e., an anti-MAL antibody) or nucleic acid probe specific for MAL may be used to detect the presence of MAL polypeptide (using antibody) or MAL polynucleotide (using nucleic acid probe) in biological fluids or tissues. Oligonucleotide primers based on any coding sequence region and regulatory sequence region in the MAL sequence are useful for amplifying DNA, for example by PCR.

When using PCR primers, nucleic acid probes or restriction endonucleases, the 5' regulatory region, first intronic sequence and coding sequence of the MAL sequence (as specified in FIG. 1) is analysed.

Any specimen containing a detectable amount of MAL polynucleotide or MAL polypeptide antigen can be used. Nucleic acid can also be analyzed by RNA in situ methods that are known to those of skill in the art such as by in situ hybridization. Preferred samples for testing according to methods of the invention include such specimens as (cervical or vaginal) scrapes, cervico-vaginal lavages or swabs, and/or (cervical) biopsies and the like. Although the subject can be any mammal, preferably the subject is human.

The invention methods can utilize antibodies immunoreactive with MAL polypeptide, the predicted amino acid sequence of which is available as GenBank Accession No. NP_002362.1, and 3 alternative transcripts NP_071883.1, NP_071884.1, NP_071885.1, or immunoreactive fragments thereof. Antibody that consists essentially of pooled monoclonal antibodies with different epitopic specificities, as well as distinct monoclonal antibody preparations can be used. Monoclonal antibodies are made from antigen containing fragments of the protein by methods well known to those skilled in the art (Kohler, et al., Nature, 256: 495, 1975).

The term antibody as used in this invention is meant to include intact molecules as well as fragments thereof, such as Fab and F (ab') 2, which are capable of binding an epitopic determinant on MAL. Antibody as used herein shall also refer to other protein or non-protein molecules with antigen binding specificity such as miniantibodies, peptidomimetics, anticalins etc.

Monoclonal antibodies can be used in the invention diagnostic methods, for example, in immunoassays in which they can be utilized in liquid phase or bound to a solid phase carrier. In addition, the monoclonal antibodies in these immunoassays can be detectably labeled in various ways. Examples of types of immunoassays that can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays that are run in either the forward, reverse, or simultaneous modes, including immunohistochemical or immunocytochemical assays on physiological samples. Those of skill in the art will know, or can readily discern, other immunoassay formats without undue experimentation.

Monoclonal antibodies can be bound to many different carriers and used to detect the presence of MAL. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

In performing the assays it may be desirable to include certain "blockers" in the incubation medium (usually added with the labeled soluble antibody). The "blockers" are added to assure that non-specific proteins, proteases, or antiheterophilic immunoglobulins to anti-MAL immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention. A number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1-100 μg/μL) may be important, in order to maintain the proper sensitivity yet inhibit any unwanted interference by mutually occurring cross-reactive proteins in the specimen.

Diagnostic methods for the detection of MAL production, MAL gene expression or disorders therein, include methods wherein a sample for testing is provided, which sample comprises a cell preparation from cervical or other tissue. Preferably such samples are provided as smears or other cytological samples.

A cell or tissue sample obtained from a mammal, preferably a human, is suitably pretreated to allow contact between a target cellular component of a test cell comprised in said sample with a reagent that detects MAL and detecting a reduction in the MAL as compared to that of a comparable normal cell. Samples may be mounted on a suitable support to allow observation of individual cells. Examples of well-known support materials include glass, polystyrene, polypropylene, polyethylene, polycarbonate, polyurethane, optionally provided with layers to improve cell adhesion and immobilization of the sample, such as layers of poly-L-lysine or silane. Cervical smears or biopsies may for instance be prepared as for the Papanicolaou (Pap) test or any suitable modification thereof as known by the skilled person, and may be fixed by procedures that allow proper access of the reagent to the target component. In certain embodiments of the invention the cytological specimens are provided as conventional smear samples or thin layer preparations of cervical cells or liquid based cytology samples or any other kind of preparation known to those of skill in the art. If storage is required, routine procedures use buffered formalin for fixation followed by paraffin embedding, which provides for a well-preserved tissue infrastructure. In order to allow for immunohistochemical or immunofluorescent staining, the antigenicity of the sample material must be retrieved or unmasked. One method of retrieving the antigenicity of formaldehyde cross-linked proteins involves the treatment of the sample with proteolytic enzymes. This method results in a (partial) digest of the material and mere fragments of the original proteins can be accessed by antibodies.

Another method for retrieving the immunoreactivity of formaldehyde cross-linked antigens involves the thermal processing using heat or high energy treatment of the samples. Such a method is described in e.g. U.S. Pat. No. 5,244,787. Yet another method for retrieving antigens from formaldehyde-fixed tissues is the use of a pressure cooker, either in combination with a microwave or in the form of an autoclave, such as described in e.g. Norton, 1994. J. Pathol. 173(4): 371-9 and Taylor et al. 1996. Biotech Histochem 71(5):263-70.

Several alternatives to formaldehyde may be used, such as ethanol, methanol, butanol, methacarn or glyoxal, citrated acetone, or fixatives may be used in combination. Alternatively, the sample may be air-dried before further processing.

In order to allow for detection with nucleic acid probes, the sample material must be retrieved or unmasked in case of formalin fixed and paraffin embedded material. One method involves the treatment with proteolytic enzymes and a post-fixation with paraformaldehyde. Proteolytic digestion may be preceded by a denaturation step in HCl. This method results in a (partial) digest of the material allowing the entry of probes to the target. No specific unmasking procedures are required in case of non-formalin fixed material, e.g. frozen material. Prior to hybridisation samples can be acetylated by treatment with triethanolamine buffer.

The nucleic acid probes or antibodies are then contacted with the sample material in a suitable buffer and permitted to specifically hybridize or bind to their nucleic acid or protein target. Upon specific binding of the nucleic acid probes or antibodies to the target components, labeled probes and/or antibodies may be detected by such methods as confocal laser scanning microscopy, bright field microscopy, flow cytometry optionally in combination with fluorescence associated cell sorting, or modifications of these techniques, which are well known to the person skilled in the art.

In one embodiment of a method of the invention an increased methylation of the MAL promoter in the test cell and/or reduced production of MAL in the test cell is detected as compared to the comparable normal cell.

The present invention also provides a kit of parts as defined in claims 19, for use in a method of detecting HPV-induced precursor lesions with invasive potential and HPV-induced invasive cancers associated with T-lymphocyte maturation associated protein (MAL) in test cells of a subject. Such a kit may suitably comprise a brush or spatula to take a (cervical) scrape together with a container filled with collection medium to collect test cells. Alternatively, a sampling device consisting of an irrigation syringe, a disposable female urine catheter and a container with irrigation fluid will be included to collect cervical cells by cervico-vaginal lavage. A kit according to the present invention may comprise primers and probes for the detection of MAL promoter methylation, or for the detection of MAL mRNA expression. In another embodiment, a kit according to the invention may comprise antibodies and reagents for the detection of MAL protein expression in cervical scrapes or tissue specimens.

A kit of parts according to the invention comprises means for the detection of MAL promoter methylation or MAL expression, such as MAL-specific antibodies, methylation-sensitive restriction enzymes, or probes or primers capable of hybridising to the nucleotide sequence of FIG. 1.

In yet another alternative embodiment of a kit of the invention the means for the detection of MAL promoter methylation or MAL expression may be combined with means for the detection of HPV infection, preferably for the detection of HPV infection of the high-risk type. Such means may comprise HPV-specific primers or probes, protein markers for HPV infection or even surrogate markers for HPV infection as are known in the art. In another alternative embodiment of a kit of the invention the means for the detection of MAL promoter methylation or MAL expression may be combined with means for the detection of CADM1 (Genbank ID NM_014333.3) promoter methylation. Detection of CADM1 promoter methylation is performed with methods similar to those use with the detection of MAL promoter methylation, as described above.

The present invention will now be illustrated by way of the following, non limiting examples.

EXAMPLES

Example 1

MAL Silencing in Cervical Carcinomas and High Grade Precursor Lesions

By micro-array expression analysis of cervical carcinomas MAL was identified as one of the most significantly down-regulated genes in cervical carcinomas compared with normal epithelial control samples.

Subsequent quantitative reverse transcriptase PCR (qRT-PCR) analysis on an independent validation set of cervical carcinomas confirmed the down regulation of MAL mRNA expression in these tumours. Reduced MAL mRNA expression was detected in 100% of cervical carcinomas (n=12) and 93% of high-grade CIN lesions (n=15), compared with 8% of normal controls (n=12). In vitro studies revealed a functional involvement of MAL inactivation in cervical cancer development, as ectopic overexpression of MAL in the HPV 16 containing cervical carcinoma cell line SiHa resulted in a reduction of proliferation and suppression of anchorage independent growth.

Example 2

Functional Role of MAL Gene Silencing in Cervical Carcinogenesis

To determine the potential functional role of MAL in cervical carcinogenesis, we stably transfected cells of the HPV16 containing cervical cancer cell line SiHa with a MAL expression vector (SiHa_MAL) or an empty control vector (SiHa (−)). Ectopic MAL expression in SiHa_MAL transfectants was confirmed by RT-PCR. Both transfectants were examined for their proliferation rate, migration capacity and ability to grow in soft agarose. SiHa_MAL transfectants showed a 43% reduction in proliferation rate as compared with SiHa (−) cells, indicating that ectopic expression of MAL has an anti-proliferative effect in vitro. Using a scratch assay we found that migration was strongly inhibited in SiHa_MAL transfectants. Moreover, SiHa_MAL cells displayed a 53% reduction in anchorage-independent growth compared with SiHa transfectants bearing the empty vector. Taken together, these data demonstrate that MAL gene silencing is an essential biological event in cervical cancer development and that re-expression of MAL in cervical cancer cells effectively represses well-established characteristics of tumor cells like proliferation, migration and anchorage independent growth.

Example 3

MAL Silencing Resulting from Promoter Hypermethylation is a Frequent Event in High Grade CIN Lesions, Cervical Squamous Cell Carcinomas, Adenosquamous Carcinomas, Adenocarcinomas and Neuroendocrine Carcinomas The fact that the MAL gene is located at 2q11-13, a chromosomal region at which we did not find recurrent chromosomal deletions in cervical cancer, prompted us to search for a potential epigenetic regulation of transcription. Treatment of cervical cancer cell lines and HPV-immortalized cell lines with methylation and histone deacetylation inhibitors resulted in a strong up-regulation of MAL mRNA expression, indicating that MAL down-regulation was indeed dependent on epigenetic control mechanisms.

Next, we analysed MAL promoter methylation in cervical tissue specimens by quantitative methylation specific PCR (qMSP) targeting two regions within the MAL promoter (i.e. −680 to −573 and −92 to −7, relative to the first ATG; referred to as M1 and M2, respectively). The housekeeping gene β-actin (ACTB) was chosen as a reference for total DNA input measurement. For all samples the quantity of measured methylated DNA was divided by the quantity of ACTB, and samples with ratios above a predefined cut-off (e.g. mean ratio normal control+2.58× standard deviation) were classified as positive.

We found that methylation of both M1 and M2 regions, hereafter referred to as dense methylation, was detectable in none of normal cervical control samples (n=22), 32% of CIN1 lesions (n=66), 80% of CIN3 lesions (n=64) and 94% of cervical squamous cell carcinomas (n=94).

Next to cervical squamous cell carcinomas we also analysed MAL promoter methylation in cervical adenocarcinomas. Adenocarcinomas, which constitute up to 20% of cervical carcinomas, are of particular interest as the incidence of cervical adenocarcinoma has remained the same or even increased in countries with a nation-wide cervical screening programme. This indicates that cervical adenocarcinoma and its glandular precursor lesion, i.e. adenocarcinoma in situ (ACIS), are frequently missed by cytology based screening. Based on comparative genetic and epigenetic studies between cervical squmaous cell carcinomas and cervical adenocarcinomas it has been found that both tumor histotypes develop via distinct carcinogenenic pathways (Dong et al., 2001, Kang et al., 2005, Wilting et al., 2006, Henken et al., 2007). Consequently, most biomarkers enabling the detection of cervical squamous cell carcinoma do not necessarily detect cervical adenocarcinoma. A well studied example is the methylation marker CADM1, showing methylation in 83% of squamous cell carcinomas but only 23% of adenocarcinoma (Overmeer et al., 2008). A second example comes from a methylation study on 9 genes (APC, DAPK1, CDH1, HLTF, hMLH1, p16, RASSF1A, THBS1 and TIMP3) showing more frequent methylation of CDH1 and DAPK1 in squamous cell carcinomas, whereas HLTF, TIMP3, RASSF1A and APC were more frequently methylated in adenocarcinoma (Kang et al., 2005). Similar results were obtained in a study analyzing the methylation of p16, APC, HIC1, DAPK, MGMT and CDH1, in which APC and HIC1 were found to be significantly more frequently methylated in adenocarcinomas, whereas on the other hand p16 and DAPK were predominantly methylated in squamous cell carcinomas (Dong et al., 2001).

Interestingly, MAL promoter methylation appeared to be an exception as, in contrast to most known markers, it detected cervical adenocarcinomas at a similar frequency as squamous cell carcinomas; i.e. 93% (26/28) of adenocarcinomas showed MAL promoter methylation at both M1 and M2 regions. Similar results have been obtained for cervical adenosquamous carcinomas and neuroendocrine carcinomas.

Therefore, MAL promoter methylation appears to be a universal methylation marker for all cervical carcinoma histotypes.

Example 4

Detection of Reduced MAL mRNA Expression and MAL Promoter Methylation in Cervical Scrapes Using a nested case-control design of women participating in a population-based screening trial we studied cervical scrapes of hrHPV positive women in which ≥CIN 2 (including 1 carcinoma) was diagnosed within 18-months of follow-up (i.e., cases) versus hrHPV positive women in whom at maximum CIN 1 was diagnosed within an 18-month follow-up period (i.e., controls). Baseline cervical scrapes of these women were collected in preservation medium in which both RNA and DNA are preserved.

Application of qRT-PCR to RNA isolated from a subset of these scrapes showed reduced MAL expression in 71% of the cases compared with 28% of the controls. Moreover, reduced MAL expression was only found in 13% (3/21) of women with hrHPV negative scrapes.

To the best of our knowledge we are the first to show the detection of mRNA down-regulation in cervical scrapes. So far, expression analysis in cervical scrapes has been restricted to up-regulated genes and mostly involved protein expression analysis rather than mRNA expression analysis, p16 being a well-studied example.

Next, methylation analysis was performed on a large series of cervical scrapes of hrHPV GP5+/6+-PCR positive women participating in population-based cervical screening in which ≥CIN 2 was diagnosed within 18 months of follow-up (Bulkmans et al., 2007; Hesselink et al., 2006). These included women with abnormal cytology (i.e. borderline dyskaryosis or worse) and normal cytology at baseline, the latter of which were discovered by a positive hrHPV test solely. In addition, hrHPV positive control women with normal cytology and CIN 1 or better within an 18-month follow-up period were included. Methylation at one or both MAL regions varied from 31% in hrHPV positive control women with normal cytology to 65% and 84% in women with ≥CIN 2 having normal and abnormal cytology at baseline, respectively. By combining the latter two groups MAL methylation was found in 79% of women with ≥CIN 2.

Example 5

MAL Promoter Methylation in Self-Sampled Specimens

We subsequently analysed self-sampled cervico-vaginal specimens collected using either a VibaBrush (Rovers Medical Devices, Oss, the Netherlands) or a Pantarhei sampler (Pantarhei Devices, Zeist, The Netherlands) during the course of a prospective study in which a total of 45,000 self-sampling packages were be sent to women who, even after a second reminder, did not respond to the invitation for regular cervical screening (See the World Wide Web address at trialregister.nl, Trial no.NTR962 (PROHTECT trial)). About one third of these women return self-sampled specimens to the lab. These samples are suitable for HPV PCR analysis (i.e. beta-globin PCR positive) and testing by hrHPV GPS+/6+-PCR yields at least as much ≥CIN 2 lesions in this population as found by regular screening in a matched population of responder women (Bais et al., Int J Cancer: 2007, 120:1505-1510).

A total of 186 hrHPV positive women without evidence of clinically meaningful disease in follow-up and 68 women with an abnormal follow-up smear and an underlying lesion ≥CIN3 were tested by qMSP for both the MAL M1 and M2 promoter regions. 62% of self-samples of women that later were diagnosed with ≥CIN3 tested positive for one or both MAL promoter regions, compared with only 28% of women without evidence of clinically meaningful disease in follow-up. These data show that MAL promoter methylation analysis on self-sampled materials is well feasible and will improve the detection of underlying high-grade cervical disease.

Example 6

Addition of CADM1 Promoter Methylation Detection to MAL Methylation Analysis in Biopsies Cervical Scrapes and Self-Sampled Specimens Aiming at increasing the sensitivity for ≥CIN2 we analysed the additive value of a second methylation marker, i.e.

CADM1 (Genbank ID NM_014333; see also Example 3), which was previously shown to be functionally involved in cervical carcinogenesis as well (Steenbergen et al., 2004; Overmeer et al., 2008).

By combining methylation analysis of the two promoter regions of MAL with one promoter region of CADM1, the number of methylation-positive high-grade CIN lesions increased from 80% to 91% (positivity was scored in case of a positive result for at least one of these regions). Conversely, adding analysis of this CADM1 region did not influence the positivity in normal cervices and low-grade CIN lesions. Adding methylation data of other genes did not markedly increase the sensitivity figures. We therefore concluded that this combination provides an optimal marker panel for ≥CIN 2/3.

By adding CADM1 (Genbank ID NM_014333) methylation analysis to cervical scrapings, 5% more ≥CIN 2 lesions were detected in women with abnormal cytology, resulting in an overall ≥CIN 2 detection rate of 83%.

Subsequent combined MAL and CADM1 promoter methylation analysis on self-sampled specimens resulted in a 69% positivity on self-samples of hrHPV positive women that later were diagnosed with ≥CIN 3. Conversely, only about one third of hrHPV positive women without evidence of clinically meaningful disease in follow-up, showed methylation for either or both markers.

After combining methylation data with hrHPV genotyping data it appeared that 84% of women diagnosed with ≥CIN 3 had CADM1 methylation, MAL methylation and/or presence of HPV 16, whereas the number of marker positive, hrHPV positive women without evidence of clinically meaningful disease in follow-up did not change markedly.

The invention claimed is:

1. A method to detect that test cells of a subject are those of an HPV-induced high-grade precancerous lesion or of HPV-induced invasive carcinoma associated with T-lymphocyte maturation associated protein (MAL),
    said method comprising measuring the expression level of the gene encoding the MAL protein; and
    detecting the level of methylation of the CADM1 promoter and/or CpG rich CADM1 genomic sequence in said test cells obtained from said subject,
        wherein a decrease in said level of expression combined with increased methylation of the CADM1 promoter and/or CpG rich CADM1 genomic sequence in said test cells as compared to normal cells detects that said cells are of an HPV-induced high-grade precancerous lesion or of an HPV-induced invasive carcinoma associated with T-lymphocyte maturation associated protein (MAL).

2. The method of claim 1, wherein said HPV-induced high-grade precancerous lesion or HPV-induced invasive carcinoma is a high-grade premalignant cervical lesion or invasive cervical cancer and said cells are cervical cells.

3. The method of claim 1, wherein said HPV-induced invasive cancer is a high-risk HPV-induced invasive cancer.

4. The method of claim 1, wherein said expression level is determined by contacting MAL transcribed RNA or MAL protein of said test cells with a reagent that detects the level of RNA encoding MAL or that detects the level of MAL protein.

5. The method of claim 4, wherein the reagent detects mRNA encoding MAL or its complement.

6. A method of detecting that test cells of a subject are those of an HPV-induced high-grade precancerous lesion or of an HPV-induced invasive carcinoma, which method comprises
    detecting an increased level of methylation of the MAL promoter and/or CpG rich MAL genomic sequence in the test cells of said subject as compared to normal cells combined with
    detecting an increased level of methylation of the CADM1 promoter in the test cells as compared to normal cells,
    wherein said combination of increased methylation levels detects that said cells are of an HPV-induced high-grade precancerous lesion or of an HPV-induced invasive carcinoma associated with T-lymphocyte maturation associated protein (MAL).

7. The method of claim 6, wherein the detecting comprises treating with a restriction endonuclease.

8. The method of claim 4, wherein the reagent is a nucleic acid probe or primer that binds to transcribed RNA encoding MAL or to its complement.

9. The method of claim 8, wherein said nucleic acid probe or primer has a detectable label.

10. The method of claim 8, wherein the nucleic acid probe has a nucleotide sequence selected from the group consisting of:
   a) a polynucleotide sequence that hybridizes under conditions of hybridization in 50% formamide, 1 M NaCl, 1% SDS at 37° C. and wash at 60° C. to the 5' regulatory region or the coding and intronic region of the MAL sequence of SEQ ID NO:1;
   b) a polynucleotide having at least 70% identity to the polynucleotide of a);
   c) a polynucleotide complementary to the polynucleotide of a); and
   d) a polynucleotide comprising at least 15 bases of a nucleotide of a) or b).

11. The method of claim 4, wherein the reagent detects MAL protein.

12. The method of claim 11, wherein the reagent is an anti-MAL antibody.

13. The method of claim 1, wherein said HPV-induced high-grade precancerous lesion or HPV-induced invasive carcinoma is of the oral cavity and said cells are oral cavity cells.

14. The method of claim 1, wherein said HPV-induced high-grade precancerous lesion or HPV-induced invasive carcinoma is of the oropharynx and said cells are of the oropharynx.

15. The method of claim 6, wherein said HPV-induced high-grade precancerous lesion or HPV-induced invasive carcinoma is a high-grade premalignant cervical lesion or invasive cervical cancer and said cells are cervical cells.

16. The method of claim 6, wherein said HPV-induced high-grade precancerous lesion or HPV-induced invasive carcinoma is of the oral cavity and said cells are oral cavity cells.

17. The method of claim 6, wherein said HPV-induced high-grade precancerous lesion or HPV-induced invasive carcinoma is of the oropharynx and said cells are of the oropharynx.

* * * * *

SEQUENCE LISTING

```
<160> NUMBER OF SEQ ID NOS: 1

<210> SEQ ID NO 1
<211> LENGTH: 2904
<212> TYPE: DNA
<213> ORGANISM: Homo sapiens

<400> SEQUENCE: 1
gactcgggcg gatttcaggc ttcagtgttt gtaggaggaa acacagcaat cacactatta      60
atagtaaatt aaaataaatg ggcaactgct gcatggtaat acttttttt ttaaggcaaa      120 aaataaaaaa tagtgaaaca gagaaacaaa acatgaaaca ccggcagtca acaggcaggc     180
aaagaacctg ggggtggggg tagcagcggt cccaccctca aaaggcccgg gctgcccaga     240
ccaagagaaa gcgatgaatc tcttctggta acgtcccttc ctgtcgcatg gattcaaggc     300
cgacctgccc cagcaccacc accagcagcc ttctgctggg gccggcacag ctgggagcaa     360
cctcctactc tcaggcagac gcgcagcacc aagcagagag gcccggtgca ggatcccagc     420
gccgaaccag cgccggctca gtggacgcgg aaggggccgg cggccgcggc cggtcccatc     480
ccccactgca gacccccagc ctgtggcggt ggtccagttc cgccaggaaa ccgccgcctg     540
gagctgtggg tcgcgcacat taacgcatcc agcggaaaaa tgaaggagac ccaaattcaa     600
agttaaagta atggtgaccc gagaggtgcc ttgatgagaa ggtttgggt cccggttact     660 gatggttatc attcttacga gatgctggtc acctacgaag ggagaaaggc acgaggagcg     720
cctgaccaaa gtggttttgc cctgcttccc gcaagaggtg gcacccacgg ctggaacgca     780
ggagtcagac ccacagtccc cagctctgga cgcccgcagc ggggcctcga agaggttcag     840
ggcggtgccc gcggcgctcg ggccgggtct cccggggcgt ggggcggggg gcggggttgg     900
gcggcggccg gggctcctcc ctcttctgcc ccgggctccc ctgctcttaa cccgcgcgcg     960
ggggcgccca ggccactggg ctccgcggag ccagcgagag gtctgcgcgg agtctgagcg    1020
gcgctcgtcc cgtcccaagg ccgacgccag cacgccgtca tggcccccgc agcggcgacg    1080
gggggcagca ccctgcccag tggcttctcg gtcttcacca ccttgcccga cttgctcttc    1140
atctttgagt ttgtgagtgg ctcctggccg gggaagggac ggggtgggct gagccgtgcg    1200
ctctctcggg cgcccagcac agctgtcgga cgggatccgc tagctgcgca ggttctggaa    1260 gcatcgggc agcaggcgca gggcgggac taagccaggg aagtcccctc ccacctccgg    1320 tccttgtgc cctcctagac caacagaatg aggggaacag tctacaggac tatggaggaa   1380
aaactgggtt cccaactggg gtcagatgta ggcagcgggg caggggggga cggctcttgg    1440
```

-continued

```
ttcgctggtc ccaaagctgc gcgcggggcc cacttgacgc gcgcagcgcc accgaagctc  1500
ccgccgcgct ttgcgcggtt gggtagaagt gcgcagcttt tacaagggag aaggtttcgt  1560
taaaaaagaa aaaaaaatca gcaagagaaa cattagtatt accaaccgag atttggagat  1620
gagagggagc tgaatccggt ttattttctt ctggccttt  aaagtttctg gcagggaac   1680
gtatttgcga ccaattcgat ctggaaatga ggccatcgtt tgcttggccg cagtccttct  1740
gccccgtgtg cggggtgggg gtggaggaga tgggggggtgg ggggtggggg gtggcggcga  1800
gagcgatccg cgcgcctcga ctgaccttgg gcaggcccgg ggcctctgca cctgcggtcg  1860
gtcccgcctt gcacgcacgg tctctgcctg aggctgcagg aaagcgcttc ctactgagaa  1920
ctcctgataa gcgctcacgg tgtcgcgaag ccgaagtgac ctccctcagc ctcaactccc  1980
cgggggccgc tggccttcac atcttcgggg gcctggtgtg gatcctggtg gcctcctccc  2040
tggtgccctg gcccctggtc cagggctggg tgatgttcgt gtctgtgttc tgcttcgtgg  2100
ccaccaccac cttgatcatc ctgtacataa ttggagccca cggtggagag acttcctggg  2160
tcaccttgga cgcagcctac cactgcaccg ctgccctctt ttacctcagc gcctcagtcc  2220
tggaggccct ggccaccatc acgatgcaag acggcttcac ctacaggcac taccatgaaa  2280
acattgctgc cgtggtgttc tcctacatag ccactctgct ctacgtggtc catgcggtgt  2340
tctctttaat cagatggaag tcttcataaa gccgcagtag aacttgagct gaaaacccag  2400
atggtgttaa ctggccgccc cactttccgg cataactttt tagaaaacag aaatgccctt  2460
gatggtggaa aaagaaaac  aaccaccccc ccactgccca aaaaaaaaag ccctgccctg  2520
ttgctcgtgg gtgctgtgtt tactctcccg tgtgccttcg cgtccgggtt gggagcttgc  2580
tgtgtctaac ctccaactgc tgtgctgtct gctagggtca cctcctgttt gtgaaagggg  2640
accttcttgt tcgggggtgg gaagtggcga ccgtgacctg agaaggaaag aaagatcctc  2700
tgctgacccc tggagcagct ctcgagaact acctgttggt attgtccaca agctctcccg  2760
agcgccccat cttgtgccat gttttaagtc ttcatggatg ttctgcatgt catgggact   2820
aaaactcacc caacagatct ttccagaggt ccatggtgga agacgataac cctgtgaaat  2880
actttataaa atgtcttaat gttc                                        2904
```